United States Patent [19]
Rubinstein et al.

[11] Patent Number: 5,595,186
[45] Date of Patent: *Jan. 21, 1997

[54] BONE MARROW BIOPSY NEEDLE

[75] Inventors: Alan Rubinstein, Los Angeles; Andrew M. Olah; Emery Olah, both of Santa Monica, all of Calif.

[73] Assignees: Alan I. Rubinstein, Los Angeles, Calif.; Daniel B. Rubinstein, Brookline, Mass.

[ * ] Notice: The term of this patent shall not extend beyond the expiration date of Pat. No. 5,462,062.

[21] Appl. No.: 400,857

[22] Filed: Mar. 8, 1995

Related U.S. Application Data

[63] Continuation-in-part of Ser. No. 863,457, Apr. 6, 1992, Pat. No. 5,462,062.
[51] Int. Cl.$^6$ ........................................................ A61B 10/00
[52] U.S. Cl. ............................................. 128/754; 128/751
[58] Field of Search ...................... 606/207, 206, 606/205, 210, 167, 170; 128/754, 751, 753, 749

[56] References Cited

U.S. PATENT DOCUMENTS

| | | | |
|---|---|---|---|
| 3,844,291 | 10/1974 | Moen | 606/206 |
| 4,427,014 | 1/1984 | Bel et al. | 128/751 |
| 4,609,370 | 9/1986 | Morrison | 604/165 |
| 4,655,226 | 4/1987 | Lee | 128/754 |
| 4,798,213 | 1/1989 | Doppelt | 128/754 |
| 5,074,311 | 12/1991 | Hasson | 128/754 |
| 5,357,974 | 10/1994 | Baldridge | 128/754 |
| 5,462,062 | 10/1995 | Rubinstein et al. | 128/754 |

*Primary Examiner*—Guy V. Tucker
*Attorney, Agent, or Firm*—Ostrolenk, Faber, Gerb & Soffen, LLP

[57] ABSTRACT

A bone marrow biopsy needle includes an outer tube having a lumen extending therethrough which narrows at the distal end of the outer tube. An inner tube is slidable through the lumen of the outer tube and includes a pair of pincers at its distal end. As the inner tube is slid through the lumen of the outer tube, the pincers will encounter the narrowed portion of the lumen and as the pincers extend beyond an opening at the distal end of the outer tube, the pincers close upon themselves, and in this manner the pincers can grasp a biopsy core from bone marrow of a patient. The pincers may have sharpened edges and/or have their edges bent radially inwardly so as to enhance the cutting of the biopsy core from the bone marrow.

12 Claims, 2 Drawing Sheets

FIG. 4
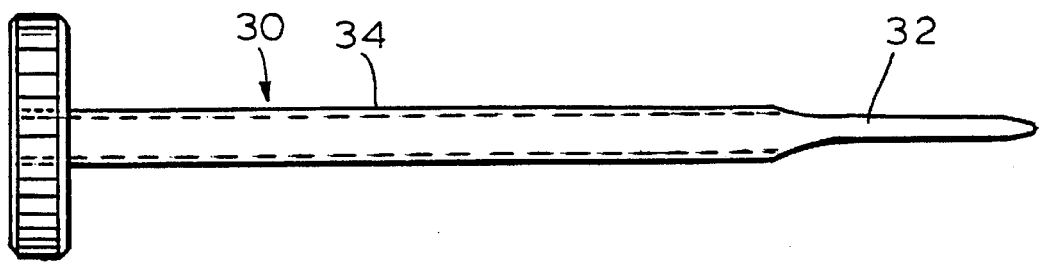
FIG. 5
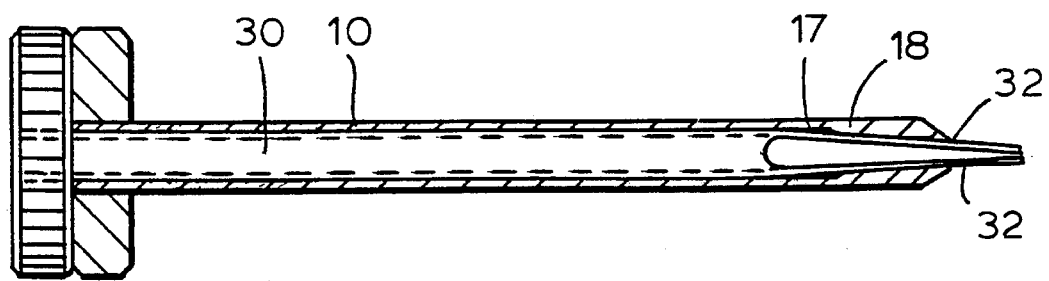
FIG. 6
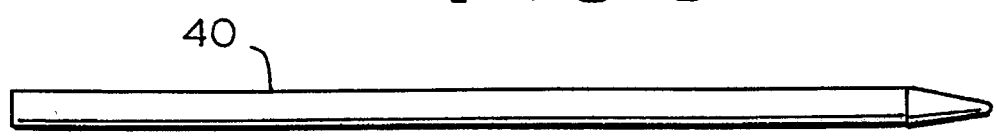
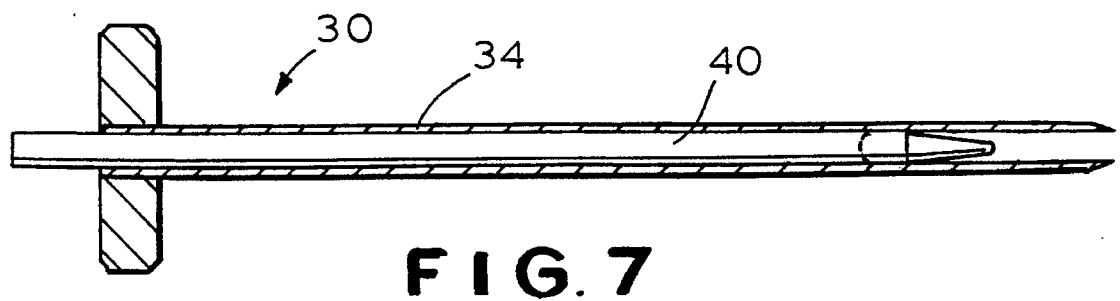
FIG. 7

BONE MARROW BIOPSY NEEDLE

CROSS-REFERENCE TO RELATED APPLICATION

This is a continuation-in-part of U.S. Ser. No. 07/863,457 filed Apr. 6, 1992, in the name of Alan I. Rubinstein and Daniel B. Rubinstein, now U.S. Pat. No. 5,462,062 the disclosures of which are expressly incorporated by reference herein.

BACKGROUND OF THE INVENTION

The present invention relates to a bone marrow biopsy needle, and more particularly to a bone marrow biopsy needle having an improved mechanism for gripping and withdrawing a biopsy core from the body of the patient.

U.S. Ser. No. 07/863,457 discloses in FIGS. 5A–5E a bone marrow biopsy needle including an outer tube with an inwardly tapered distal end, and an inner tube with a pair of opposed blades hinged to the inner tube at its distal end. The inner tube is slidable axially within the outer tube. The taper at the distal end of the outer tube defines a dead space radially outward of the needle opening. The blades have an open position in which they are contained within the dead space.

The outer tube is inserted into the bone being biopsied with the blades retracted into the dead space so as not to obstruct the entry of the biopsy into the space within the outer and inner tubes. The outer tube is sharp, as is customary, so as to enter the bone easily. Then, when the biopsy has entered the needle, the inner tube is pressed axially in the distal direction. The blades engage the tapered end of the outer tube, which folds them radially inward on their hinges, simultaneously cutting off the biopsy core and retaining it in the needle. A detent and blocking arrangement is provided for holding the inner and outer tubes in various relative positions.

Although the above-described needle is effective and greatly improves the ease and security of the bone marrow biopsy process, it would be desirable to make further improvements by reducing the number of moving parts and assembly steps required to manufacture the needle. More particularly, it would be desirable to simplify the hinge arrangement, as well as the detent and blocking arrangement.

SUMMARY OF THE INVENTION

It is accordingly an advantage of the present invention to provide a bone marrow biopsy needle which has fewer moving parts than the above-described prior needle.

A further advantage of the inventive needle is that it is more economical and simpler to manufacture than the prior needle.

According to a preferred embodiment of the invention, a bone marrow biopsy needle may comprise an outer tube having a lumen extending therethrough, and a proximal end and a distal end with an opening at the distal end. The lumen of the outer tube narrows at the opening at the distal end. An inner tube is adapted to slide in the lumen of the outer tube. The inner tube includes pincers at its distal end, which are used for receiving and grasping a biopsy core from bone marrow of a patient. As the pincers extend through the narrowed lumen at the distal end of the outer tube, the narrowed lumen causes the pincers to close and grasp, just forward of the distal end of the outer tube, a biopsy core of the bone marrow of a patient.

The pincers may have sharpened edges and/or the edges may be bent radially inwardly so as to enhance the cutting action of the pincers as they grasp a biopsy core from the bone marrow.

Other features and advantages of the present invention will become apparent from the following description of a preferred embodiment of the invention, with reference to the accompanying drawings.

BRIEF DESCRIPTION OF THE DRAWINGS

FIG. 4 is a side view of the inner tube;

FIG. 5 is a plan view, partly in cross-section, showing the inner tube inserted into the outer tube;

FIG. 6 is a plan view of a push rod which forms a further part of the embodiment; and FIG. 7 is a plan view showing the push rod inserted into the inner tube.

DETAILED DESCRIPTION OF THE EMBODIMENT

Figure 1:
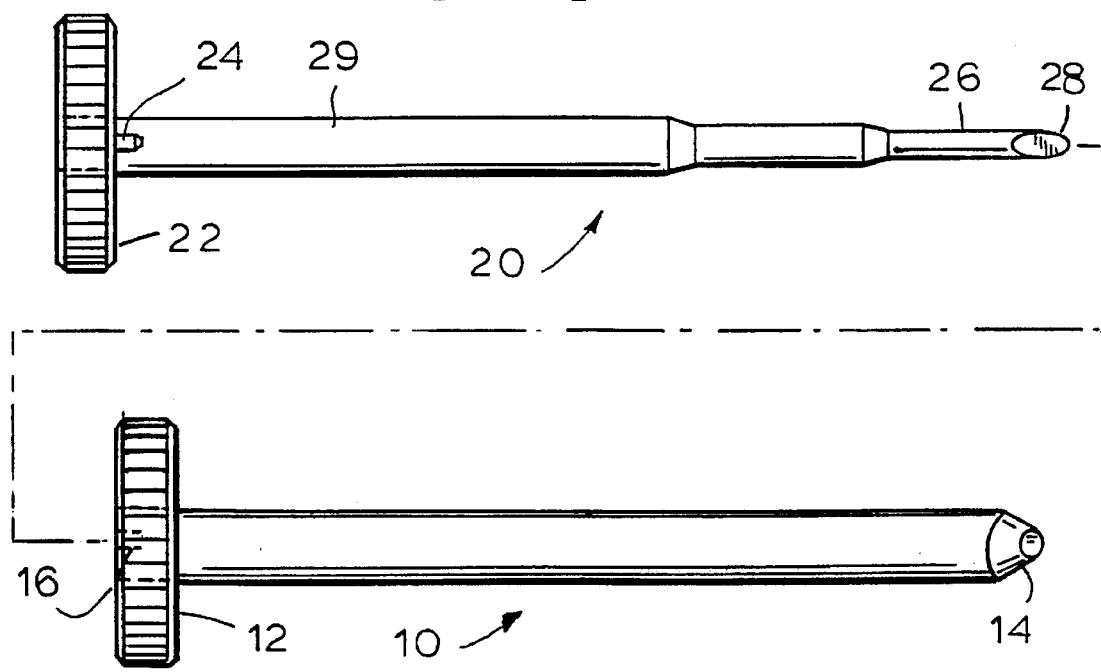
FIG. 1 is a plan view of an outer tube and a stylet which form part of the embodiment.
Figure 2:
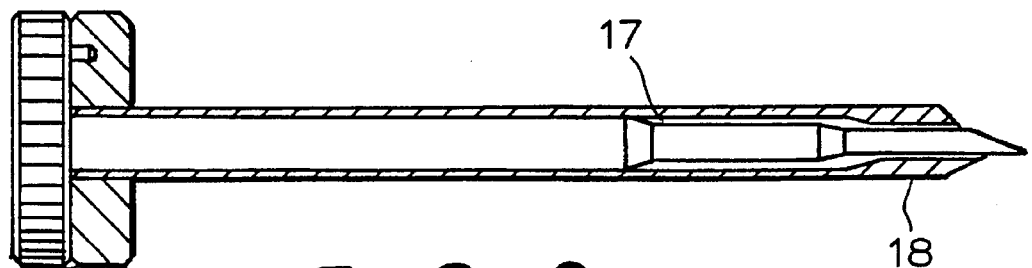
FIG. 2 is a plan view, partly in cross-section, showing the stylet inserted into the outer tube.

FIG. 1 and 2 show an outer tube 10 and a stylet 20. The outer tube 10 has a knurled control knob 12 at its proximal end and a taper 14 at its distal end. The stylet 20 has a knurled control knob 22 with a locating pin 24 adapted for being inserted into a recess 16 in the control knob 12 to prevent relative movement during the stylet process.

The stylet 20 has a narrow portion 26 at its distal end with a bevelled chisel end 28 formed therein. As best seen in FIG. 2, when the stylet is fully inserted into outer tube, the narrow portion 26 is accommodated closely with a narrowed portion 18 of the lumen 17 of the outer tube, with the chisel end 28 slightly projecting out of the outer tube 10. The stylet 20 also has a proximal end 29 which is sized for being closely accommodated within the proximal end of the outer tube. The close engagement of the stylet 20 and the outer tube 10 contributes to minimizing their relative movement during the stylet process.

The bevel angle of the chisel end 28 is advantageously similar to or the same as the taper angle of the taper 14 of the outer tube, in order to form a continuous or substantially continuous distal surface which is generally cone-shaped. The cone-shaped distal surface enables the combination of the outer tube and the stylet to enter into the bone being biopsied with maximum smoothness and with the distal end being closed. If the surfaces of the taper 14 and the chisel end 28 did not substantially line up, the discontinuity between them would increase the difficulty of the needle entering the bone.

It would be obvious to the skilled practitioner that other types of stylet can be used in carrying out the present invention. In particular, stylet 20 may be similar or identical to the stylet incorporated in the conventionally known Jamshidi Bone Marrow BX Needle.

In use, the outer tube 10 and the stylet 20 are engaged as shown in FIG. 2 in order to be inserted into the bone. After the outer tube 10 and stylet 20 have been inserted into the bone marrow, the stylet 20 is withdrawn from outer tube 20, leaving the outer tube in the bone marrow. Next, the inner tube 30 is inserted into the outer tube 10 in order to take the bone marrow biopsy.

Figure 3:
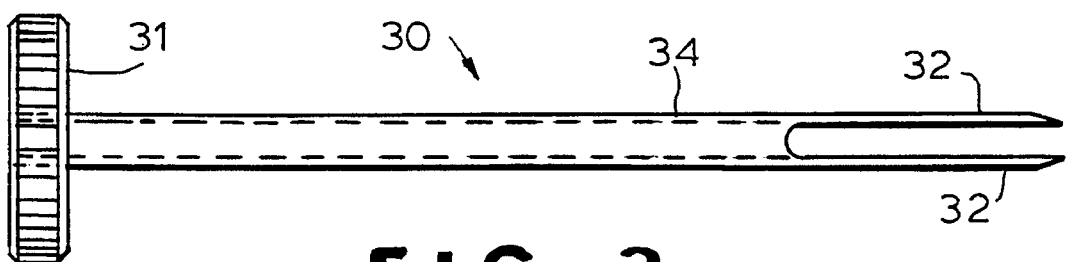
FIG. 3 is a plan view of an inner tube which forms a further part of the embodiment.

As seen in FIG. 3, the inner tube 30 has a control knob 31 at a proximal end and a pair of pincers 32 at a distal end. The pincers 32, shown in side view in FIG. 4, are substantially narrower than the rest of the inner tube 30, so as to be able to pass through the narrowed portion 18 of the outer tube 10. The inner tube 30 has a hollow lumen 34 extending along its entire length, including through the control knob.

FIG. 5 shows the position of the inner tube 30 after being inserted into the outer tube 10. As shown here, the inner tube in this embodiment is long enough for the pincers to project out of the outer tube when the inner tube has been fully inserted into the outer tube. As they are being inserted, the pincers 32 engage the narrowed portion 18 and are thereby urged radially inward and together, pinching off and grasping a sample of bone marrow just forward of the distal end of the outer tube. The pincers 32 may have sharpened edges and/or their edges may be bent radially inwardly, so as to enhance the cutting action. The pincers 32 may be two opposed blades which are tapered at their distal ends, i.e., tweezer-like in structure. To ensure cut-off from surrounding bone marrow, both the outer tube 10 and inner tube 30 may be rotated, i.e., 180° to 380°. This procedure, however, may not be necessary. Then the outer and inner tubes 10, 30 are withdrawn together from the bone, with the narrowed portion 18 continuing to hold the pincers 32 together in order to hold the sample during the process of withdrawal.

After withdrawal, if desired, a push rod 40, shown in FIG. 6, may be employed as shown in FIG. 7 to expel the bone marrow sample distally out of the inner tube 30. The push rod 40 is sized to closely fit the lumen of the inner tube 30, and may have a cone-like distal end to enhance displacement of a bone marrow sample from the inner tube 30.

Although a preferred embodiment has been described herein, many other variations and modifications and other uses will become apparent to those skilled in the art within the fair spirit and scope of the invention. The present invention, therefore, is not limited by the specific disclosure herein.

What is claimed is:

1. A bone marrow biopsy needle for removing bone marrow from a patient, comprising in combination:

an outer tube member having a lumen therein, a proximal end and a distal end and an opening at said distal end, said lumen narrows proximate to the opening; and an inner tube member adapted to be slidable in said lumen of said outer tube member, said inner tube member having pincers at a distal end thereof, said pincers capable of being slidable in said outer tube member, said pincers capable of closing by flexing relative to said inner tube it and said inner tube slide in the direction from the proximal end to the distal end of said outer tube and engage the narrowed lumen proximate to said opening of said outer tube member, and thereby said pincers being adaptable to grasp a biopsy core when said needle is inserted into the bone marrow of a patient.

2. A bone marrow biopsy needle as in claim 1, wherein said pincers include two opposed blades being tapered at their distal ends.

3. A bone marrow biopsy needle as in claim 1, wherein said pincers being tweezer-like in structure.

4. A bone marrow biopsy needle as in claim 1, wherein said pincers has sharp edges, and thereby being capable of enhancing the cutting of a biopsy core from the bone marrow of a patient.

5. A bone marrow biopsy need as in claim 1, wherein said pincers have edges being bent radially inwardly, and thereby capable of enhancing the cutting of a biopsy core from the bone marrow of a patient.

6. A bone marrow biopsy needle as in claim 1, wherein the distal end of said outer tube member being tapered.

7. A bone marrow biopsy need as in claim 1, wherein said inner tube member and said pincers being unitary in structure.

8. A bone marrow biopsy needle as in claim 1, wherein along an axis of the inner tube member, said pincers being narrower than the remaining portion of said inner tube member so as to be able to pass through the narrowed position of said lumen of said outer tube member.

9. A bone marrow biopsy needle as in claim 1, wherein said inner tube member having a lumen therethrough.

10. A method of removing a biopsy core of a patient using said bone marrow biopsy needle of claim 1, comprising the steps of:

inserting said outer tube and said inner tube into a patient;

grasping with said pincers of said inner tube a biopsy core of bone marrow;

closing said pincers about said biopsy core of bone marrow by sliding said pincers through the narrowed lumen of said outer tube; and cutting off said biopsy core of bone marrow.

11. A method of removing a biopsy core of bone marrow as in claim 10, further comprising the steps of:

rotating said outer tube and said inner tube to ensure the cutting off of said biopsy core of bone marrow.

12. A bone marrow biopsy needle as in claim 1, wherein said pincers are capable of closing as it extends from said opening of the outer tube member, and said pincers are capable of grasping a biopsy core forward of said distal end said outer tube member.

* * * * *